United States Patent [19]

Darnell

[11] Patent Number: 4,807,845

[45] Date of Patent: Feb. 28, 1989

[54] TUBE VALVE

[75] Inventor: Larry W. Darnell, Cypress, Tex.

[73] Assignee: Kardiothor, Inc., The Woodlands, Tex.

[21] Appl. No.: 103,058

[22] Filed: Sep. 30, 1987

[51] Int. Cl.[4] ............................................... F16K 7/07
[52] U.S. Cl. ........................................... 251/7; 251/5
[58] Field of Search ................................. 251/4, 5, 7, 9

[56] References Cited

U.S. PATENT DOCUMENTS

| | | | |
|---|---|---|---|
| 3,145,713 | 9/1963 | Lathan, Jr. | 128/214 |
| 3,244,363 | 3/1963 | Hein | 233/28 |
| 3,384,336 | 5/1968 | Pulman | 251/9 |
| 3,408,034 | 10/1968 | Lau | 251/9 |
| 3,634,228 | 10/1969 | Latham, Jr. | 210/21 |
| 3,650,296 | 3/1972 | Johnson et al. | 251/9 X |
| 3,942,228 | 3/1976 | Buckman et al. | 251/4 |
| 4,086,924 | 5/1978 | Latham, Jr. | 128/214 |
| 4,151,844 | 5/1979 | Cullis et al. | 128/214 |
| 4,425,113 | 1/1984 | Bilstad | 251/9 X |
| 4,425,116 | 1/1984 | Bilstad et al. | 251/7 X |
| 4,460,358 | 7/1984 | Somerville | 251/7 X |
| 4,549,860 | 10/1985 | Yakich | 417/475 |
| 4,684,361 | 8/1987 | Feldman et al. | 494/41 |
| 4,692,136 | 9/1987 | Feldman et al. | 494/38 |

FOREIGN PATENT DOCUMENTS

WO85/02561 6/1985 World Int. Prop. O. .

OTHER PUBLICATIONS

"Cell Saver 4", Haemonetics Corporation, 1984—Autologous Blood Recovery System with Tube Valves.

"Packed Cells in 3 Minutes", Haemonetics Corporation, dated prior to 1986—Tube Valves, p. 3.

"Haemonetics", Instructions for Haemonetics Corporation Unit, dated prior to 1986—Blood Processor Instruction, particularly paragraphs 11-17 dealing with tubing and clamping.

"BRAT TM ", Kardiothor, Inc. 1986—tube valves.

Primary Examiner—A. Michael Chambers
Assistant Examiner—John C. Fox
Attorney, Agent, or Firm—Vaden, Eickenroht, Thompson & Boulware

[57] ABSTRACT

A tube valve, an actuator mechanism for a tube valve, a jaw for a tube valve, and a tube valve assembly including all of them. In one embodiment the tube valve has a valve body and a jaw movably mounted thereon, the jaw suitable for holding hollow flexible tubing and moving it into operative contact with a valving member for providing valving action of closing-off and opening-up the tubing to the flow of fluid therethrough. The valving member may be movably disposed through the valve body so that it can be moved into and out of operative contact with the tubing while the jaw is in position about the plunger. A latch assembly may be provided for holding the jaw in position about the plunger. In one embodiment the latch assembly includes a neck and a shaft attached thereto, the neck pivotably mounted to the valve body so that it can be pivoted to move the shaft into a holding recess in the jaw. The actuator mechanism has a lever member pivotably mounted to a housing. At one end of the lever member an air cylinder is movably connected to provide force to pivot the lever member. The valve plunger is connected to a rod which is pivotably mounted to the other end of the lever member so that energizing of the air cylinder retracts the plunger thereby opening up the tubing to flow therethrough. A tube valve assembly according to the present invention may have singly or in combination the above-described tube valve, jaw, and actuator mechanism.

3 Claims, 7 Drawing Sheets

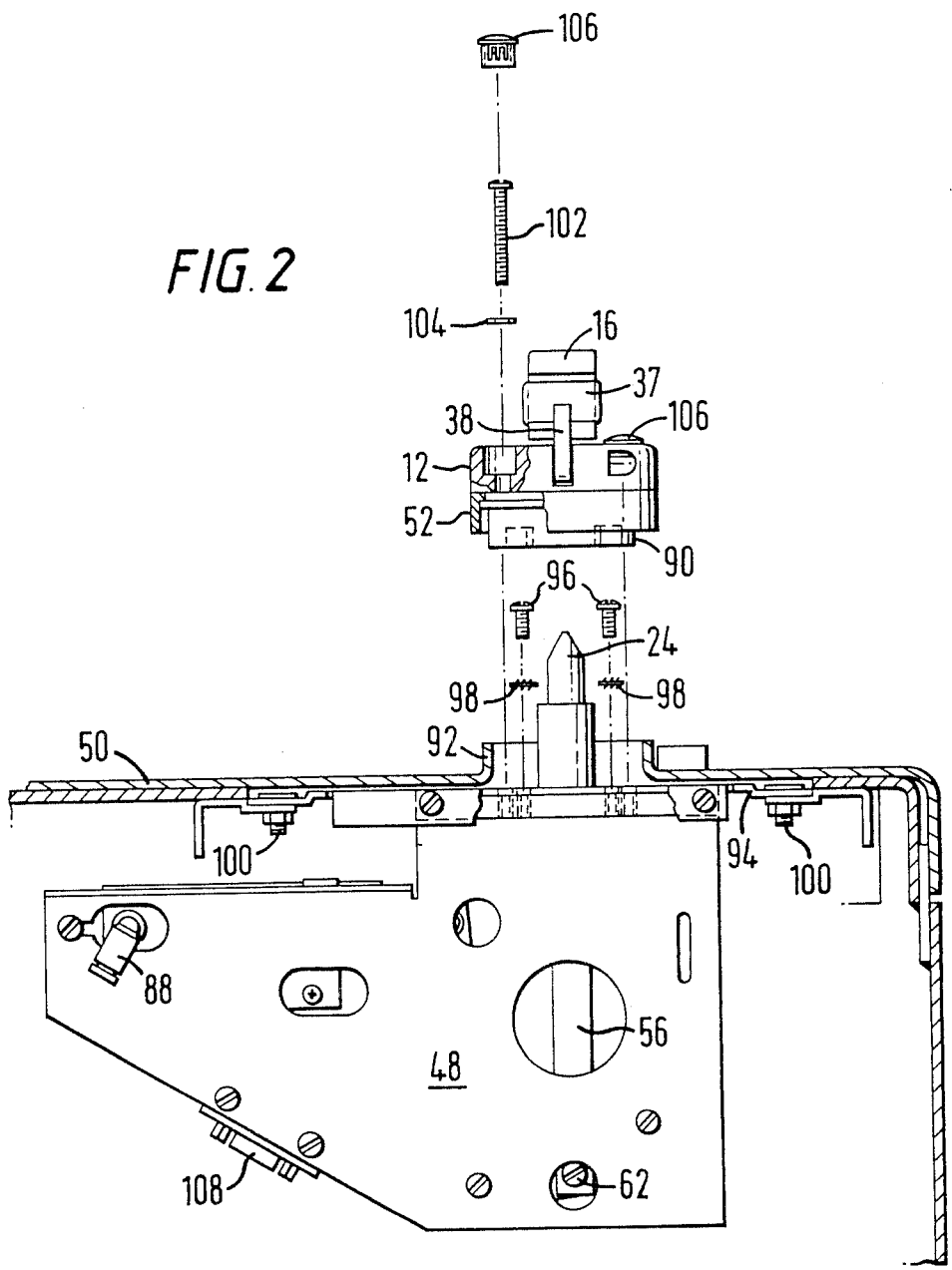

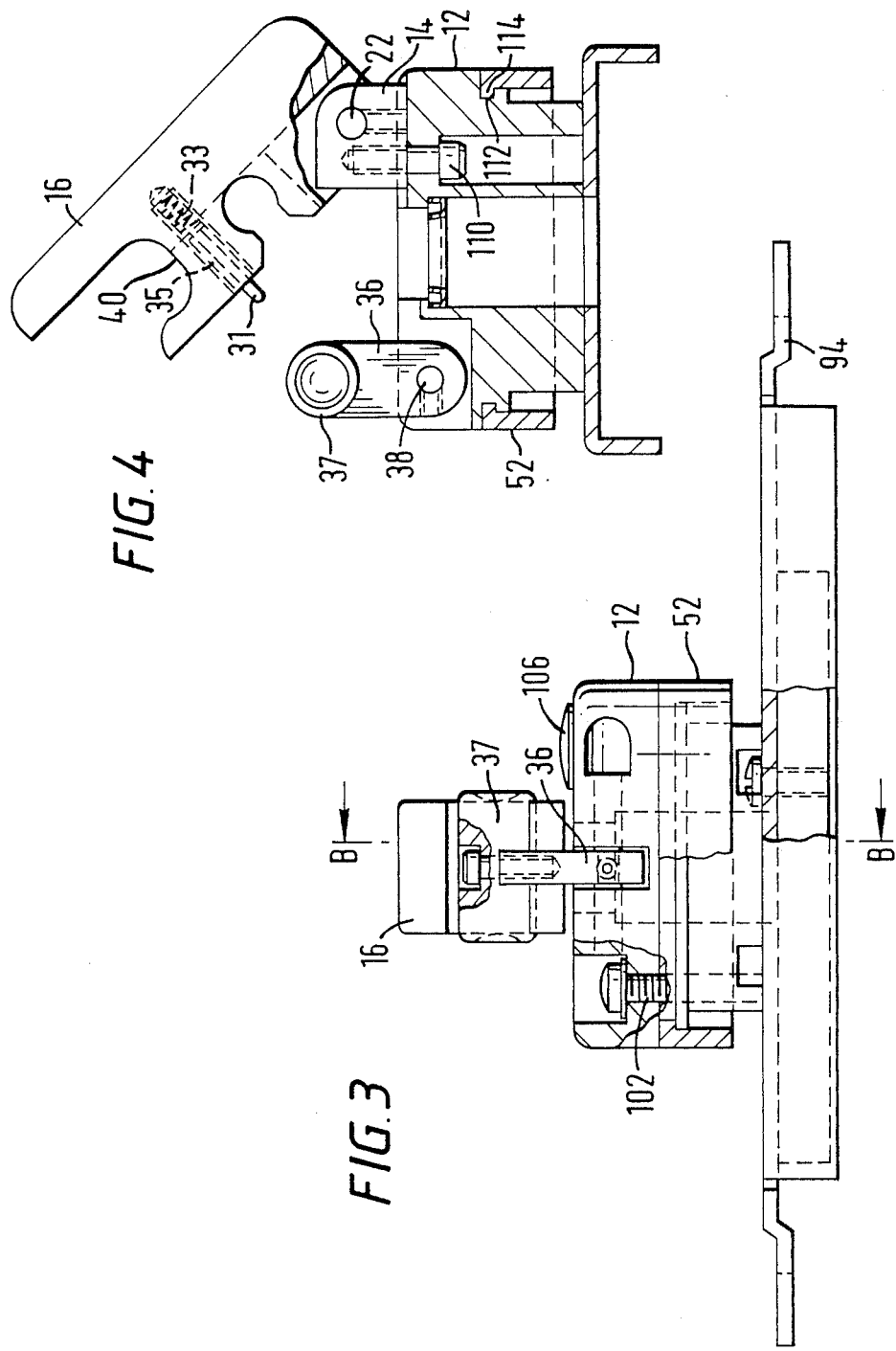

TUBE VALVE

BACKGROUND OF THE INVENTION

1. Field of the Invention

This invention is directed to a tube valve, to an actuator mechanism for a tube valve, and to a jaw for holding tubing. One specific embodiment of a tube valve according to this invention is for a valve for tubing used in blood transfusion systems.

2. Description of the Prior Art

Prior art tube valves have included valves with a fixed holding member for holding tubing placed therein and a movable valving member or plunger which is pushed against the tubing to pinch it together, thereby preventing flow through the tubing. In order to open this prior art valve, i.e. to release the plunger so that flow through the tubing is resumed, air supplied by an air compressor is used to activate a movable member connected to the plunger thereby retracting it and opening the valve. Any problem rendering the air compressor inoperative resulted in an inoperative valve. A variety of leakage problems are also associated with this prior art valve. When an extending push button is used to activate the plunger, there is a leakage path around the push button. If the button is mounted near or above other mechanisms or electrical or electronic components, severe problems ensue when these elements are subjected to the leaked fluid being pumped. Other areas of leakage include the interface between a base for the valve and a cabinet panel or top to which it is mounted and the non-sealed area around the movable plunger. When working with blood or saline solutions being transmitted through tubing, a leak onto computerized circuits used to control a blood transfusion system can be disastrous.

Correct installation and routing of tubing in a typical blood transfusion system is a complex task. In a typical auto-transfusion system disposable sets of flexible plastic tubing are used in the form of a multi-branch line which flows into a single trunk line. Tube valves control each of the branch lines. Such systems use spring-loaded closed valve designs, particular for instances of power failure or machine failure. Set-up of such a system done in a powered-down mode requires that the operator must open the valve against spring force and insert tubing into each branch. A certain amount of adjustment is necessary to insure that the tubing is properly positioned. The valve's plunger had to be depressed (i.e. moved out of pinching contact with the tubing) in order to install or remove tubing. In the case of a power failure, the actuating mechanism could be depressed manually by the operator to open the valve. Such manual operation would require an operator to hold the actuating mechanism down with one hand with sustained force so that the plunger would be maintained in the depressed position while adjusting the tubing's position with the other hand, then often having to repeat the sequence several times until the tubing was set properly.

Since the prior art valves are spring-loaded-closed often with relatively large force against soft plastic tubing, occlusion of the tubing of varying degrees occurs.

Without admitting that anything disclosed is analogous, pertinent, or prior art, in accordance with 37 C.F.R. §1,56 the following are disclosed:

| U.S. Pat. Nos. | |
| --- | --- |
| 4,692,136 | Blood centrifuge with which present tube valve is useful |
| 4,684,361 | Blood centrifuge with which present tube valve is useful |
| 4,549,860 | Blood pump |
| 4,151,844 | Blood separator |
| 4,086,924 | Plasmapharesis apparatus |
| 3,634,228 | Centrifuge with flow lines with clamps (items 13, 26 in the Figure) |
| 3,244,363 | Centrifuge apparatus with complex flow lines |
| 3,145,713 | Blood processor |
| PCT Application WO 85/02561 | Disposable centrifuge with forceps or hemostat clamps for flow lines (FIG. 13; text p. 13 top) |
| Publications | |
| "Cell Saver 4", Haemonetics Corporation, 1984 | Autologous blood recovery system with tube valves |
| "Packed Cells in 3 Minutes" Haemonetics Corporation, dated prior to 1986 | Tube valves, p.3 |
| "Haemonetics", instructions for Haemonetics Corporation unit, dated prior to 1986 | Blood processor instructions, particularly paragraphs 11–17 dealing with tubing and clamping. |
| "BRAT TM" Kardiothor, Inc., 1986 | Tube valves |

Applicant considers U.S. Pat. No. 3,634,228; PCT Application WO 85/02561; and the above-listed publications to be more relevant then the other listed references. Applicant's assignee is the owner of U.S. Pat. Nos. 4,692,136 and 4,684,361. Applicant's assignee was previously known as Cardiovascular Systems, Inc. and is the manufacturer of the BRAT TM transfusion system described in the above-listed "BRAT TM" brochure.

There has long been a need for an efficient tubing valve which does not leak; in which tubing is easily installed; which does not require a sustained force by the operator to hold it open; which does not occlude tubing; and which can be easily operated in a manual mode.

SUMMARY OF THE INVENTION

The present invention is directed to a tube valve, to an actuator mechanism for a tube valve, and to a jaw for holding tubing. A valve according to this invention includes a valve body and a jaw member movably attached to the valve body. The jaw member has a tubing opening therethrough which acts as a built-in clip in the jaw for holding tubing to be acted on by the valve. A sealing member extends from the valve body for contacting and closing off the tubing. The jaw member is rotatably mounted to the valve body so that it can be rotated into position over the sealing member in such a position that the sealing member contacts and pushes against the tubing extending through the jaw member's tubing opening thereby closing off the tubing to the flow of fluid therethrough.

In another embodiment the jaw member can have a latch shaft recess therein for receiving and holding a latch assembly so that the valve can be maintained with the tubing closed off. The latch assembly can have a latch neck pivotably connected to the valve body and a latch shaft secured to the latch neck. The jaw member's latch shaft recess is configured to receive the latch shaft upon rotation of the jaw member toward the valve body and pivoting of the latch assembly toward the jaw member. An outwardly-urged detent mounted in the valve body or in the jaw member can be disposed to push outwardly against an adjacent member to assist in maintaining the latch assembly's shaft in the recess in the jaw member. The latch assembly is disengaged by pivoting the latch assembly away from the jaw member, thereby freeing the latch shaft from the jaw member's latch shaft recess. The latch neck can be configured to avoid contact with the jaw member upon pivoting of the latch assembly; or the jaw member may have a latch neck recess therein for receiving the latch neck. In another embodiment these parts can be reversed with the latch assembly pivotably connected to the jaw member and with a recess or recesses in the valve body for receiving the latch shaft or latch neck or both.

In another embodiment the sealing member may be a plunger movably dispossed through a plunger recess in the valve body. A movable plunger may be provided with means for either manual operation, automatic operation or both. In one embodiment an actuator mechanism is used to move the plunger in the plunger recess. The actuator mechanism includes an L-shaped lever member. The plunger is pivotably connected to the lower horizontal portion of the L-shaped lever member. The L-shaped lever member itself is pivotably mounted to a housing in which the tube valve is mounted so that the L-shaped lever member is pivotable about a point through the area where the two members of the L-shaped lever member meet. The end of the horizontal member spaced apart from the end where it meets the vertical member has means for affixing thereto a spring which is also connected to the housing. The spring urges the plunger toward the valve body and jaw member to provide a spring-loaded-closed feature. The upper end of the vertical member of the L-shaped lever member is pivotably connected to an air cylinder's piston. Introducing air into the air cylinder pushes the piston outwardly causing the L-shaped lever member to rotate about the point where it is pivotably connected to the housing, thereby lowering the horizontal member of the L-shaped lever member and causing the plunger attached thereto to be moved out of and away from the valve body and jaw member, thus opening the valve and permitting flow through the tubing. Of course where the plunger is pressed against the tubing shutting off flow therethrough, rotation of the jaw member away from the valve body also results in the breading of contact between the plunger and the tubing so that fluid flows through the tubing.

Seals, either dynamic or static, may be employed to preclude the passage of unwanted fluid through or around the valve into a cabinet or other housing in which the valve is mounted; i.e., seals may be provided around the plunger between the plunger and the valve body; around the valve body between the valve body and the housing; and around various screws used to attach parts of the valve together. A feedback sensor may be used to convey the position of the valve (open or closed) to the operator. In one embodiment the sensor provides valve position information for a computerized memory diagnostic that is performed initially each time the apparatus with the valve (or valves) is powered up.

In order to install or remove tubing, an operator unlatches the jaw member, opening the valve. To install tubing, the operator snaps the tubing into the tubing opening in the jaw member. The position of the tubing is easily adjusted longitudinally by moving it back and forth. Upon closing of the jaw member and latching, the tubing is contacted and compressed by the plunger. This can all be done with one hand and while the plunger is biased in a closed-valve position. If the jaw member of a valve is not latched close, this is apparent at a glance and can easily be noticed by an operator.

The present invention, therefore, recognizes, addresses, and satisfies the long-felt needs for an efficient and accurate tube valve, actuator for a tube valve, and jaw for holding tubing.

It is therefore an object of the present invention to provide a novel, efficient, useful, and nonobvious tube valve.

It is therefore an object of the present invention to provide a novel, efficient, useful, and nonobvious actuator mechanism for a tube valve.

It is therefore an object of the present invention to provide a novel, efficient, useful and nonobvious jaw for holding tubing.

Another object of this invention is the provision of a tube valve having a jaw for holding tubing pivotably connected to a valve body for pivotable movement into valving contact with a fixed sealing member or movable plunger to close off tubing held in the jaw.

A further object of the present invention is the provision of a pivotable, easily manipulable latch assembly for securing the jaw to the valve body or vice versa.

An additional object of this invention is the provision of an actuator mechanism for opening a tube valve by moving a plunger used therein for closing off flow through tubing. A particular object of the present invention is the provision of such a mechanism which is spring-loaded-closed.

Yet another object of the present invention is the provision of such tube valves which are sealed at critical points.

These and other objects of this invention including objects inherent therein to one of skill in this art who has the benefit of this invention's teachings which include the drawings and the following description of presently-preferred embodiments of the invention which are given for the purpose of disclosure in accordance with the patent laws of the United States.

BRIEF DESCRIPTION OF THE DRAWINGS

FIG. 2 is a partial side cross sectional view of the apparatus of FIG. 1.

FIG. 3 is a front view of parts of the tube valve of FIG. 1. FIG. 3 is taken along line A—A of FIG. 5.

FIG. 4 is a side view of part of the device of FIG. 3, taken along line B—B of FIG. 3.

DESCRIPTION OF PRESENTLY PREFERRED EMBODIMENTS

Figure 1:
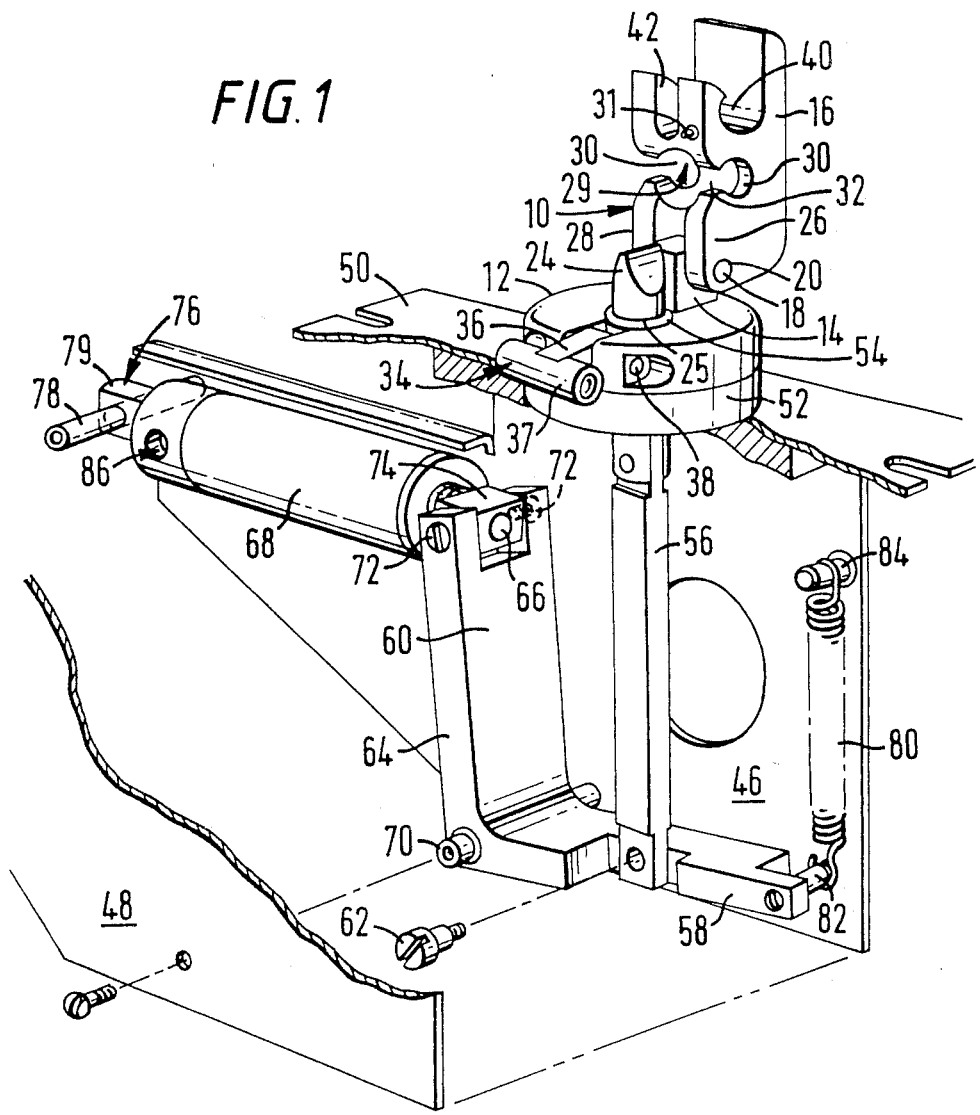
FIG. 1 is an isometric view, partially cutaway, of a tube valve with an actuator mechanism according to the present invention.

As illustrated in FIG. 1, a tube valve 10 has a valve body 12 to which is secured a block 14. A jaw 16 is pivotably connected to the block 14 by a jaw shaft 18 extending through holes 20 in the jaw and a corresponding hole 22 (FIG. 4 in the block 14). The jaw 16 can pivot downwardly toward a plunger 24 disposed in a plunger hole 26 through the valve body 12.

The jaw 16 has two jaw block members 26 and 28 for mounting of the jaw 16 about the pivot block 14. Formed in each jaw block member is a tubing recess 30 with a mouth 32 communicating with the recess 30. The mouth 32 is slightly smaller in size than the recess 30. The recess 30 is sized to hold tubing. The tubing can be pushed through the mouth 32 into the opening 30. The smaller size of the mouths 32 prevents the tubing from falling out of the openings 30.

Rotation of the jaw 16 downwardly about the shaft 18 brings the tubing in the jaw into contact with the plunger 24. When the jaw 16 has been moved to a nearly horizontal position the plunger 24 will have compressed the tubing closed, preventing flow through the tubing.

Figure 5:
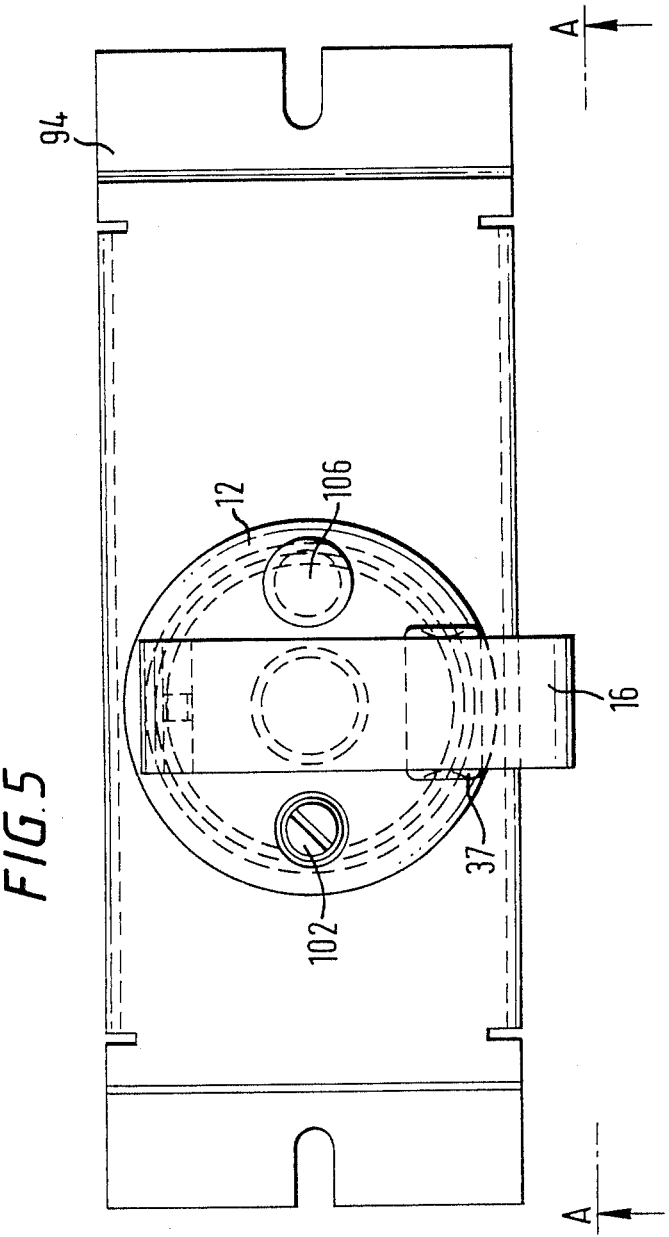
FIG. 5 is a top plan view of the device of FIGS. 3 and 4.

To maintain the closing contact between the jaw and the plunger a latch assembly 34 is provided. A latch neck 36 is pivotably mounted to the valve body 12 by a shaft 38 running through the valve body 12 and the latch neck 36 (FIGS. 4 and 5). The jaw 16 has a latch shaft recess 40 for receiving and holding the latch knob 37 upon pivoting of the latch assembly toward and into the jaw 12. A latch neck recess 42 in the jaw 12 receives the latch neck 36 so that movement of the latch knob 37 into the latch shaft recess 40 is not impeded. A detent or spring plunger 31 is movable disposed within a recess 35 within the jaw 16 and urged outwardly by a spring 33 disposed there about. The plunger 31 contacts the top f the valve body 12 and, since the spring 33 pushes on the plunger 31, the jaw 16 is pushed slightly upwardly with a continuous force which serves to maintain the knob shaft 37 in the recess 40 when the tube valve is closed. Of course a similar detent could be provided in the valve body to push against an adjacent portion of the jaw to achieve the same effect.

The valve 10 is mounted to a housing having a side plate 46, a side plate 48 and a top plate 50 secured to each side plate. A seal 52 is disposed between the valve body 12 and the top plate 50.

A seal 54 is disposed about the movable plunger 24. The plunger 24 is secured to a plunger rod 56 which is in turn pivotably connected to the lower horizontal member 58 of an L-shaped lever member 60 by means of a pivot screw 62 which holds the rod 56 in place and permits it to pivot. An upper vertical member 64 of the lever member 60 of the lever member 60 is pivotably connected to a piston rod 66 of an air cylinder 68 by the pivot screw 72. The lever member 60 is pivotably connected to the side plate 46 by the connecting rod 70. The piston rod 66 is connected to a block 74 by two screws 72, one on each side of the lever member 60 (only one side shown in FIG. 1). An air inlet 86 provides a coupling juncture for an air coupling 88 (FIG. 2) for introducing compressed air into the air cylinder 68. One end 76 of the air cylinder 68 is anchored between the two side plates 46 and 48 by an anchor pin 78 extending through a block 80 which is connected to the air cylinder 68. The block 80 (and therefore the air cylinder 68) are movable about the anchor pin 78.

A spring 80 is connected to a rod 82 secured to and extending from the member 58 and to a rod 84 secured to and extending from the side plate 46. The spring 80 is an extension spring which urges the member 58 upwardly thereby urging the plunger 24 into closing contact with tubing in place in the tubing recesses 30.

As shown in FIG. 2, the valve body 12 is formed with a depending portion 90 for insertion into an upwardly extending lip 92 of the top plate 50. The seal 52 (preferably made of urethane) is disposed between the valve body 12 and the top plate 50 and it contacts the upwardly extending lip 92. A sheet metal bracket 94 connected to the top plate 50 with screws 100 provides a member to which the valve body 12 is mounted by screws 96 (preferably stainless steel binding head screws) and lock washers 98. Two or more screws 102 are used to secure the valve body 12 to the bracket 94. These screws are preferably stainless steel binding head screws and are used with a washer seal 104 such as a commercially available Parker Stat-O-Seal. The holes through which the screws 102 are inserted can be sealingly capped with a hole plug 106. A feedback device connection 108 is provided for connecting thereto the internal feedback device provided with commercially available conventional air cylinders such as the Humphrey 6SPI Air Cylinder or air cylinders made by the Bimba Company. The device indicates whether the valve is open or closed.

As shown in FIG. 3 the latch shaft 38 is in place in the recesses 30 of the jaw 16. As shown in FIG. 4 the jaw 16 has been raised a screw 110 holds the block 14 to the valve body 12. A groove 112 in the valve body 12 is formed to receive a lip 114 of the seal 52 to hold the seal 52 in place.

Figure 6:
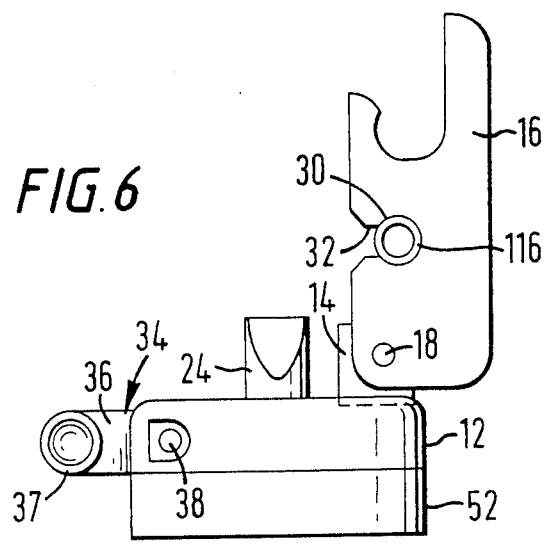
FIGS. 6, 7, and 8 are side views (FIGS. 7 and 8 partially in cross section) showing a sequence of operation of a jaw according to this invention as shown in FIG. 1.
Figure 7:
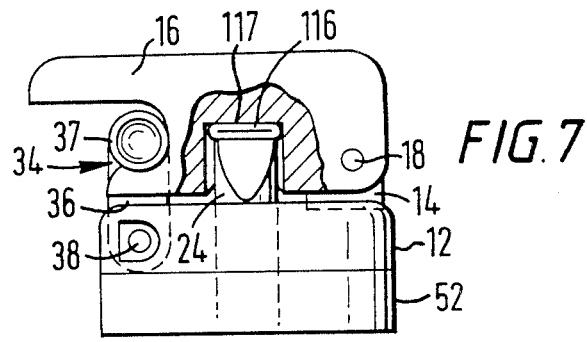
Figure 8:
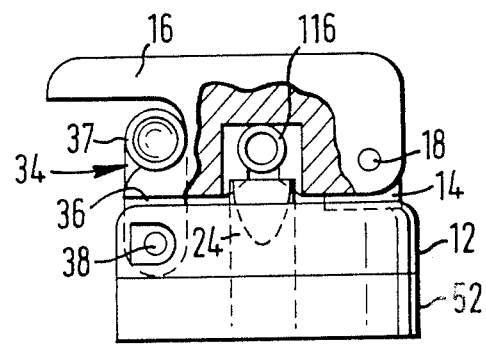
Figure 9:
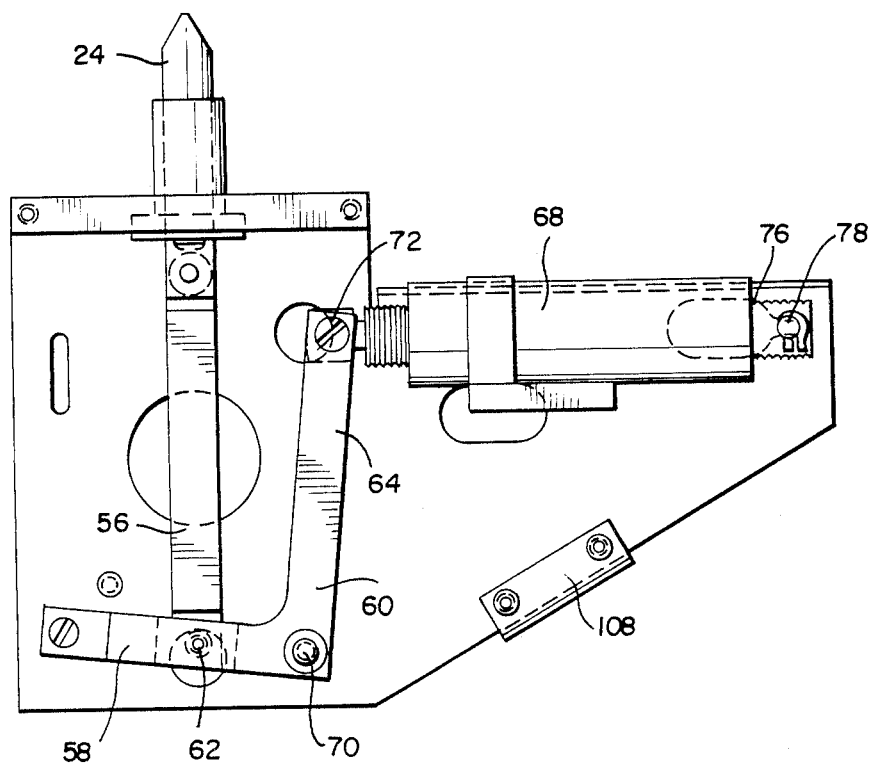
FIG. 9 is a side view of the actuator mechanism shown in FIG. 1.

FIGS. 6-8 represent a sequence of operation of the tube valve 10 according to this invention. As shown in FIG. 6, a piece of tubing 116 has been snapped through the mouths 32 and into the recesses 30 of the jaw 16. The plunger 24 is in the up position and the latch assembly 34 is not engaged by the jaw 16. As shown in FIG. 7, the jaw 16 has been pivoted downwardly bringing the tubing 116 into closing contact with the plunger 24. The latch shaft 38 has been moved into the recess 40 and is holding the jaw in the horizontal position with the tubing closed. As shown in FIG. 8, the plunger 24 has been retracted, opening the tubing 116, with the latch assembly 34 still engaged by the jaw 16. In this embodiment the air cylinder is automatically powered up or down by small interface valves which are activated by microprocessors. The small valves control the flow of compressed air to the air cylinders of the tube valves. The cylinder could be mounted vertically or almost vertically near the plunger, eliminating the need for the lever member or it could be mounted vertically with the plunger on one end of the piston.

Thus, it is seen that the apparatuses and methods of the present invention readily achieve the ends and advantages mentioned as well as other inherent therein. While certain preferred embodiments of the present invention have been described and illustrated for the purposes of disclosure, it will be clear to one of skill in this art who has the benefits of this invention's teachings that changes in the arrangement and construction of parts and steps may be made which changes are embodied within the spirit and scope of the present invention as claimed below. It is intended that each combination of elements is to be understood as referring to all equivalent elements or equivalent combinations for accomplishing substantially the same results in substantially the same or equivalent manner.

What is claimed is:

1. A tube valve for providing valving action of closing off and opening up hollow flexible tubing placed in the valve, the valve comprising a valve body, a seal mounted about the valve body for providing sealing between the valve body and a mounting plate to which the valve body is mounted, a jaw pivotably connected to the valve body, the jaw comprising a main body member having first opening therein for receiving and holding the hollow flexible tubing, the body member having a second opening therein communicating with the first opening and permitting the insertion therein of a plunger to contact and act upon the hollow flexible tubing, and the body member having a third opening smaller than the first opening yet sufficiently large for the hollow flexible tubing to be pushed therethrough, the third opening communicating with the first opening so that the tubing can be pushed through the third opening into the first opening, the third opening preventing the tubing from becoming disengaged from the first opening, a movable plunger projecting from the valve body for contacting the hollow flexible tubing and closing it off to a flow of fluid therethrough, the movable plunger disposed through a hole in the valve body, the movable plunger movable into and out of contact with the hollow flexible tubing thereby closing or opening up the tubing to the flow of fluid, the jaw movable to bring the hollow flexible tubing held therein into contact with the valving member, a movable latch assembly for holding the jaw in position about the plunger, the movable latch assembly comprising a latch neck pivotably mounted to the valve body, a latch shaft connected to the latch neck, the latch shaft receivable within a latch shaft recess formed in the jaw, the latch shaft insertable in the latch shaft recess upon pivoting of the jaw to a position about the plunger, and an actuator mechanism for the movable plunger, the mechanism comprising a pivotable L-shaped lever member having a generally upwardly extending first member and a generally sideways extending second member, the lever member pivotably mounted to the housing about the area where the first and second members meet, a connecting rod pivotably mounted to the second member and secured to the plunger an air cylinder having two ends and secured to the housing at one of its ends, the other of its ends having an air piston extending therefrom, the piston movably disposed within the air cylinder and movable in response to air introduced under pressure into the air cylinder, the air piston pivotably connected to the first member of the lever member so that the introduction of air into the air cylinder causes the piston to be moved outwardly, this in turn causing the lever member to pivot with its second member moving downwardly, thereby retracting the connecting rod and the attached plunger.

2. A tube valve for providing valving action of closing off and opening up hollow flexible tubing, the valve comprising a valve body a jaw pivotably connected to the valve body, the jaw having a jaw opening therethrough for receiving and holding the hollow flexible tubing, a valving member projecting from the valve body and movable into the jaw opening for contacting the hollow flexible tubing within the jaw and closing the tubing off to a flow of fluid therethrough, the jaw movable to move the valving member into the jaw opening to contact the hollow flexible tubing held therein, and a movable latch assembly means for holding the jaw in position about the valving member, the movable latch assembly means comprising a latch neck pivotably mounted to the valve body, a latch shaft connected to the latch neck, the latch shaft receivable and holdable within a latch shaft recess formed in the jaw, the latch shaft insertable in the latch shaft recess upon pivoting of the jaw to a position about the valving member.

3. An actuator mechanism for a movable valving plunger for a tube valve, the tube valve for providing valving action of the plunger for closing off and opening up hollow flexible tubing placed in the valve, the actuator mechanism mounted to a housing, the valve having a valve body disposed outside of the housing for receiving and holding the tubing, the actuator mechanism comprising an L-shaped lever member pivotably mounted in the housing, the plunger connected to the lever member and movably extending through the valve body and movable into and out of contact with the tubing outside of the housing, and a power means connected to the lever member for pivoting the lever member and thereby moving the plunger, the lever member having a generally upwardly extending first member and a generally sideways extending second member, the lever member pivotably mounted in the housing about the area where the first and second members meet, and including a connecting rod pivotably mounted to the second member and secured to the plunger, the plunger movably extending through the valve body and the connecting rod movable to move the plunger into contact with the tubing outside of the housing, an air cylinder having two ends and secured to the housing at one of its ends, the other of its ends having an air piston extending therefrom, the piston movably disposed within the air cylinder and movable in response to air introduced under pressure into the air cylinder, the air piston pivotably connected to the first member of the lever member so that the introduction of air into the air cylinder causes the piston to be moved outwardly, this in turn causing the lever member to pivot with its second member moving downwardly, thereby retracting the connecting rod and the attached plunger, and an extension spring connected to the second member of the lever member and to the housing at a point above the second member, the spring pulling up on the second member and thereby forcing the connecting rod and its attached plunger upwardly to maintain the tube valve in a spring-loaded-closed position.

* * * * *